US012005003B2

(12) United States Patent
Caddell

(10) Patent No.: US 12,005,003 B2
(45) Date of Patent: Jun. 11, 2024

(54) MULTIFUNCTION MEDICAL PLATFORM

(71) Applicant: Carol Caddell, Henrico, VA (US)

(72) Inventor: Carol Caddell, Henrico, VA (US)

( * ) Notice: Subject to any disclaimer, the term of this patent is extended or adjusted under 35 U.S.C. 154(b) by 818 days.

(21) Appl. No.: 17/076,462

(22) Filed: Oct. 21, 2020

(65) Prior Publication Data
US 2021/0113404 A1 Apr. 22, 2021

Related U.S. Application Data

(60) Provisional application No. 62/924,424, filed on Oct. 22, 2019.

(51) Int. Cl.
A61G 12/00 (2006.01)
A61M 5/14 (2006.01)
A61M 16/08 (2006.01)
A61M 27/00 (2006.01)
B62B 3/02 (2006.01)
B62B 3/04 (2006.01)
B62B 3/10 (2006.01)
B62B 5/00 (2006.01)
B62B 5/06 (2006.01)

(52) U.S. Cl.
CPC ......... A61G 12/001 (2013.01); A61G 12/008 (2013.01); A61M 5/1415 (2013.01); A61M 27/00 (2013.01); B62B 3/02 (2013.01); B62B 3/04 (2013.01); B62B 3/106 (2013.01); B62B 5/00 (2013.01); B62B 5/06 (2013.01); A61M 16/0875 (2013.01); A61M 2209/084 (2013.01)

(58) Field of Classification Search
CPC . A61G 12/001; A61G 12/008; A61M 5/1415; A61M 27/00; A61M 16/0875; A61M 2209/084; B62B 5/00; B62B 5/06; F16M 11/28; F16M 11/42
See application file for complete search history.

(56) References Cited

U.S. PATENT DOCUMENTS 4,332,378 A * 6/1982 Pryor ................. A61M 5/1415
211/205
4,407,475 A * 10/1983 Gossage ............... A47B 37/04
108/5

(Continued)

FOREIGN PATENT DOCUMENTS

CN 201333221 Y 10/2009
CN 204106709 U 1/2015

(Continued)

OTHER PUBLICATIONS

PCT International Search Report and Written Opinion in International Application No. PCT/US2020/056592, mailed Feb. 11, 2021.

Primary Examiner — Anita M King
(74) Attorney, Agent, or Firm — NIXON PEABODY LLP

(57) ABSTRACT

A medical platform is disclosed that can fulfill numerous functional and practical needs of patients and caregivers in a single, simple assembly. The medical platform disclosed herein can replace many of the different medical apparatuses used in a healthcare facility. The combination of features as disclosed herein can permit the medical platform to facilitate patient mobility by combining multiple commonly-used and/or required apparatuses into a single, mobile platform.

18 Claims, 9 Drawing Sheets

(56) References Cited

U.S. PATENT DOCUMENTS

| | | | | |
|---|---|---|---|---|
| 5,337,992 | A | * | 8/1994 | Pryor .................... A61G 7/0503 |
| | | | | 248/219.2 |
| 5,947,351 | A | * | 9/1999 | Garofalo .................. A45F 3/04 |
| | | | | 294/169 |
| 7,748,672 | B2 | * | 7/2010 | Walke .................. A61G 13/107 |
| | | | | 248/207 |
| 7,935,030 | B1 | | 5/2011 | Nesbitt |
| 8,613,454 | B2 | * | 12/2013 | Foley ................... B25H 1/0007 |
| | | | | 280/32.6 |
| 9,033,162 | B2 | * | 5/2015 | Brotzman ............... A61B 50/20 |
| | | | | 211/126.14 |
| D733,891 | S | * | 7/2015 | Murray ........................ D24/185 |
| 2009/0050756 | A1 | | 2/2009 | Newkirk et al. |
| 2009/0294604 | A1 | * | 12/2009 | Sunderland ............ F16M 11/42 |
| | | | | 248/227.3 |
| 2015/0327935 | A1 | | 11/2015 | Coleman et al. |
| 2017/0361013 | A1 | | 12/2017 | Koehler |

FOREIGN PATENT DOCUMENTS

| | | |
|---|---|---|
| CN | 204655651 U | 9/2015 |
| CN | 109847144 A | 6/2019 |

\* cited by examiner

MULTIFUNCTION MEDICAL PLATFORM

CROSS REFERENCE TO RELATED APPLICATIONS

The present application claims the benefit of U.S. Provisional Patent Application 62/924,424 filed Oct. 22, 2019 and entitled "MULTIFUNCTION MEDICAL PLATFORM," which is hereby incorporated by reference in its entirety.

TECHNICAL FIELD

The present disclosure relates to medical equipment generally and more specifically to ambulatory hospital equipment.

BACKGROUND

In many medical environments, such as hospitals, various pieces of medical equipment may be used in the treatment or medical intervention of a patient, whether on an acute basis or over the course of an extended period of time. Often, such medical equipment can be cumbersome and ungainly, making it difficult for patients to move from where the medical treatment is being administered.

For some of these patients, it can also be important to permit the patient to be able to move around, such as walk around a room or a floor of a medical facility. Such ambulatory freedom can be important to a patient's physical and psychological outcome, especially when hospitalized for extended periods of time. Additionally, the ability for a patient to move around freely can facilitate the healthcare staff's ability to treat the patient.

Thus, certain ambulatory devices, such as rolling intravenous (IV) poles exist to permit a user to carry an IV bag with them at an appropriate height while simultaneously being treated from the IV bag. However, existing ambulatory devices, such as IV poles, are limited to only specific functions and are unable to help patients undergoing medical interventions with more complex medical equipment or more complex combinations of medical equipment.

SUMMARY

The term embodiment and like terms are intended to refer broadly to all of the subject matter of this disclosure and the claims below. Statements containing these terms should be understood not to limit the subject matter described herein or to limit the meaning or scope of the claims below. Embodiments of the present disclosure covered herein are defined by the claims below, supplemented by this summary. This summary is a high-level overview of various aspects of the disclosure and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this disclosure, any or all drawings and each claim.

Embodiments of the present disclosure include a medical platform, comprising: a base having a plurality of legs; a set of casters, each caster of the set of casters being coupled at a distal region of a respective leg of the plurality of legs of the base; a support pole extending vertically from the base, the support pole movable between a compressed position and an extended position; an upper assembly coupled to the support pole, the upper assembly having a plurality of vertical poles extending away from the base and a plurality of hooks coupled to top ends of the plurality of vertical poles; and a tray assembly coupled to the support pole between the base and the upper assembly, the tray assembly having a stationary tray portion and a deployable tray portion, the deployable tray portion movable between a stowed position and a deployed position; a catheter collection bag hook coupled to one of the support pole and the tray assembly at or below the stationary tray portion, wherein the catheter collection bag hook is positioned to maintain a catheter collection bag at or below a waist level of a patient during ambulation; and a hand bar coupled to one of the support pole and the tray assembly.

In some cases, the base further includes a central bar having a first end and a second end, wherein the support pole extends from the central bar, wherein the plurality of legs includes a first pair of legs and a second pair of legs, wherein the first pair of legs extends distally and collinearly from the first end of the central bar, and wherein the second pair of legs extends distally and collinearly from the second end of the central bar. In some cases, the medical platform further comprises a deployable footrest movable between a deployed position and a stowed position; and a footrest securement feature coupled to the support pole, wherein the footrest securement feature is usable to secure the footrest in the stowed position. In some cases, the deployable footrest includes a footrest surface for supporting a foot of a patient when the footrest is in the deployed position, wherein the deployable footrest is movable such that the footrest surface is in a substantially vertical position when the deployable footrest is in the stowed position; and wherein the deployable footrest, when in the deployed position, contacts at least one of the plurality of legs to pass force applied to the footrest surface to the at least one of the plurality of legs.

In some cases, the tray assembly is coupled to the support pole such that movement of the support pole from the compressed position to the extended position increases the distance from the base to the tray assembly. In some cases, a distance between an outer edge of the hand bar and support pole is greater than a distance between the support pole and the distal end of each of the plurality of legs. In some cases, the support pole comprises: an inner pole positioned within an outer pole; and a hydraulic actuator usable to extend and retract the inner pole out from and into the outer pole to move the support pole between the compressed position and the extended position. In some cases, the hand bar forms a semi-circular shape opposite the support pole from the tray assembly. In some cases, the medical platform further comprises a chest tube collection device hook coupled to the stationary tray portion of the tray assembly, wherein the chest tube collection device hook is shaped to receive a handle of a chest tube collection device. In some cases, the catheter collection bag hook is coupled to the support pole using an adjustable collar, wherein the adjustable collar permits the catheter collection bag hook to be raised or lowered along a length of the support pole between the base and the tray assembly. In some cases, the medical platform further comprising a gas canister retention strap positioned on the support pole between the base and the tray assembly for securing a gas canister to the support pole.

In some cases, each vertical pole of the plurality of vertical poles of the upper assembly includes an upper pole positioned within an opening of a lower pole, the lower pole positioned between the upper pole and the base, wherein the upper pole is movable within the opening to adjust a length of the vertical pole, and wherein at least one of the plurality of hooks is coupled to a top end of the upper pole. In some cases, the upper assembly includes: a crossbar coupled to the support pole, wherein at least one of the plurality of vertical poles is coupled to the crossbar; and a circular support surface positioned on the crossbar, the circular support surface having a diameter greater than a length of the crossbar, wherein the circular support surface includes a lip that extends towards the base such that a bottom surface of the lip is vertically positioned between a bottom surface of the crossbar and the base.

Embodiments of the present disclosure include a medical platform system comprising: a base having a friction reducing element to facilitate translating the base along a floor; an extendable support pole coupled to the base; a hand bar coupled to the support pole to facilitate translating the base along the floor; a deployable tray assembly coupled to the support pole such that extension of the extendable support pole increases a distance between the deployable tray assembly and the base; and an upper assembly coupled to the support pole, the upper assembly including at least one vertical pole, the at least one vertical pole having a hook positioned at an upper end of the vertical pole for receiving an intravenous bag.

In some cases, a distance between the upper assembly and the deployable tray assembly remains constant during extension of the extendable support pole. In some cases, the at least one vertical pole is extendable such that a distance between the hook and the deployable tray assembly is adjustable separately from a distance between the deployable tray assembly and the base.

In some cases, the base includes: a central bar having a first end and a second end, wherein the support pole is perpendicularly coupled to the central bar; and a set of legs extending perpendicular to the central bar at opposite ends of the central bar, wherein the set of legs and the central bar form a pair of opposing U shape voids, wherein a first void of the pair of opposing U shape voids is positioned opposite the central bar from a second void of the pair of opposing U shape voids; wherein the friction reducing element includes a set of casters, wherein each caster of the set of casters is positioned at a distal end of a respective leg of the set of legs. In some cases, the hand bar forms a semi-circular shape that extends over the first void of the pair of opposing U shape voids, wherein a center axis of the semi-circular shape is laterally centered above a center axis of the first void of the pair of opposing U shape voids; and wherein a center axis of the tray assembly is laterally centered above a center axis of the second void of the pair of opposing U shape voids.

In some cases, the at least one vertical pole comprises a pair of vertical poles, and wherein the tray assembly extends from the support pole in a direction parallel a line between the pair of vertical poles. In some cases, the medical platform system further comprises a deployable footrest movable between a deployed position and a stowed position, wherein the deployable footrest includes a footrest surface for supporting a foot of a patient when the footrest is in the deployed position, wherein the deployable footrest is movable such that the footrest surface is in a substantially vertical position when the deployable footrest is in the stowed position; wherein the deployable footrest is securable in the stowed position by a footrest securement feature coupled to the support pole; and wherein the deployable footrest, when in the deployed position, contacts the base to pass force applied to the footrest surface to the base.

BRIEF DESCRIPTION OF THE DRAWINGS

The specification makes reference to the following appended figures, in which use of like reference numerals in different figures is intended to illustrate like or analogous components.

DETAILED DESCRIPTION

Figure 1:
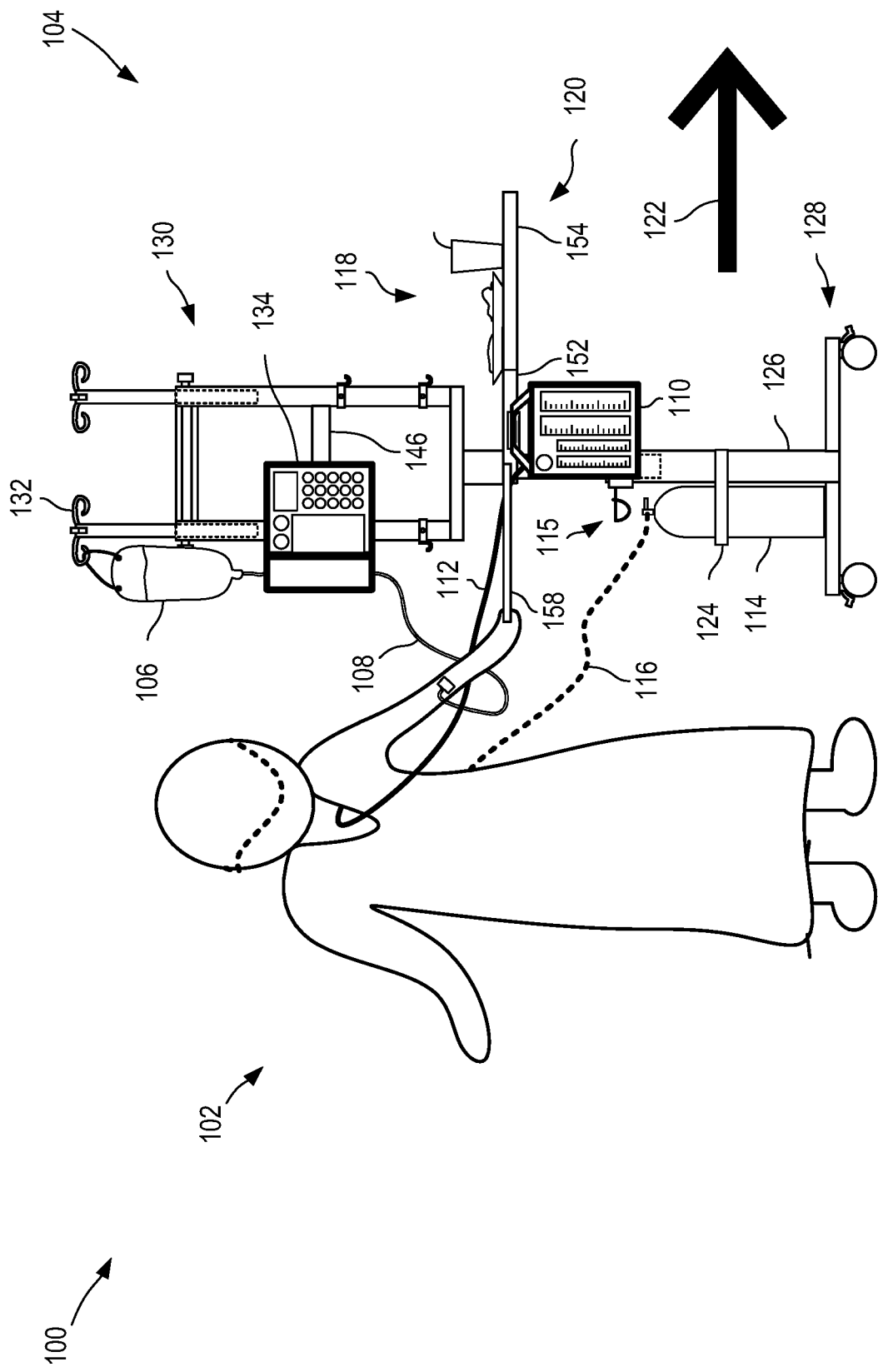
FIG. 1 is a schematic diagram depicting a patient using a multifunction medical platform according to certain aspects of the present disclosure.

Certain aspects and features of the present disclosure relate to a medical platform designed to fulfill numerous functional and practical needs of patients and caregivers in a single, simple assembly. The medical platform disclosed herein can replace many of the different medical apparatuses used in a healthcare facility. The combination of features as disclosed herein are especially useful and can permit the medical platform to facilitate patient mobility by combining multiple commonly-used and/or required apparatuses into a single, mobile platform that is easy and safe to use by both patients and medical professionals.

The medical platform can be supported on a movable based (e.g., a base with sliding elements, wheels, and/or casters) and can operate as a pushcart. The platform can include a support pole (e.g., central pole) coupled to a base. In some case, the support pole can include multiple poles or other supports, although generally only a single support pole is used. The support pole, or other supports, can be vertically extendable, moving from a compressed position to an extended position. The support pole, or other supports, can be hydraulically extendable for ease of use, although other actuators can be used to extend and/or contract the support pole. The support pole can be round in shape, although that need not always be the case.

The medical platform has a base that can include wheels and/or casters to facilitate movement of the platform. The platform can include one or more locking wheels, which can lock to ensure stability of the platform and to help minimize the risk of a patient falling when holding onto the platform. The locking wheels can provide a stable base for confused patients, such as those suffering from Dementia, thus preventing the platform from being accidentally pulled forcefully into the patient by the patient, or prevent the platform from rolling away when a patient uses the platform to stand. Additionally, the locking wheels can help prevent a confused patient from wondering off. The base can be made in an H shape with 4 wheels, although other shapes can be used.

The base can include static and/or deployable footrests, such as one or more footrests that can fold down into place for use or fold up when not in use. The footrests can provide additional support to a patient when standing or sitting near the platform. In some cases, the footrests can elevate the feet of patients suffering from heart failure or those experiencing swelling.

The platform can include a tray system for supporting items of a patient or caregiver, such as a meal. The tray system can include a deployable tray portion capable of being deployed to an extended length. The deployable tray portion can deployed in a planar fashion (e.g., radially from the center pole of the platform) or can fold at a hinge (e.g., fold up from a vertical position to a horizontal position). The tray system can include any number of supports or locking mechanisms to secure the deployable tray portion in the deployed position. In some cases, the tray system can be movably attached to the center pole for individual vertical adjustment. In some cases, however, the tray system can be fixedly attached to the center pole, which can be separately adjusted vertically to adjust the vertical position of the tray system.

In some cases, one or more hooks can be positioned at or under the tray system, such as to hold a collection bag (e.g., urine collection bag) of a catheter, such as a Foley catheter. The position of such hooks at or under the tray system can help keep the collection bag below the patient's bladder to aid in proper drainage. Such a hook can be known as a collection bag hook, a catheter collection bag hook, or a urine collection bag hook, and can be coupled to the support pole, to the tray system, or otherwise. In some cases, the collection bag hook can be positioned on an adjustable collar for vertical adjustment along the support pole along a length that lies between the base and the tray assembly.

In some cases, a hand bar can be placed at or near the tray system to provide a handhold for patients ambulating with the platform. In some cases, the hand bar can be extended from the center pole sufficiently far to minimize the patient's contact with the base (e.g., to minimize accidental kicking of the wheels).

In some cases, the top of the medical platform can include an upper platform design to hold one or more intravenous (IV) bags. In some cases, the upper platform can include two vertical poles, each including a set of IV hooks. In some cases, each of the vertical poles can hold four IV bags on individual IV hooks. The height of the vertical poles can be separately extendable to place the IV bags at an optimal height to reduce the risk of medication errors. The poles can permit IV bags to stay at ideal elevations while also not blocking the view of a patient using the platform. In some cases, clips or other mechanical features can help secure tubing associated with the IV bags to the upper platform to keep the tubing organized.

In some cases, an adjustable bar can be positioned between the vertical poles to support an IV pump. The adjustable bar can be movably and adjustable vertically, thus permitting ideal placement of the IV pump to facilitate proper placement and routing of IV bags and promote proper routing of IV tubing to the patient. In some cases, the adjustable bar and/or other portions of the upper platform can include a blocking material designed to block lights of the IV pump from view by a patient to promote better sleep for the patient and reduce distractions.

In some cases, the upper platform can include one or more accessory hooks. In some cases, the placement of the one or more accessory hooks on the upper platform can facilitate proper placement of medical equipment, such as placement of a pleura vacuum routed to chest tubes of a patient. In some cases one or more of the accessory hooks can be sized and/or positioned to accept a pleura vacuum in a desired position.

Overall, the design and combination of elements of the disclosed platform can facilitate various patient functions. For example, the platform can facilitate patient mobility, permitting the patient to get up and move around (e.g., to promote proper blood flow after surgeries and medical procedures). The use of the disclosed hand bar can permit patient to walk around without accidentally kicking the wheels or base. The use of the upper portion can permit IV bags and other IV equipment to be used without blocking the view of the patient as the patient ambulates with the platform. The tray system permits the platform to replace other bedside trays that might otherwise occupy space in the healthcare facility.

In some cases, various components of the disclosed platform can be made of a material designed to prevent the spread of various infections. In some cases, the tray system and/or deployable tray table can be made of a material designed to prevent the spread of certain infections, such as Clostridium difficile (C. diff). In some cases, the tray system and/or deployable tray table can be made of copper or a copper alloy, such as to prevent the spread of C. diff.

These illustrative examples are given to introduce the reader to the general subject matter discussed here and are not intended to limit the scope of the disclosed concepts. The following sections describe various additional features and examples with reference to the drawings in which like numerals indicate like elements, and directional descriptions are used to describe the illustrative embodiments but, like the illustrative embodiments, should not be used to limit the present disclosure. The elements included in the illustrations herein may not be drawn to scale.

FIG. 1 is a schematic diagram 100 depicting a patient 102 using a multifunction medical platform 104 according to certain aspects of the present disclosure. The platform 104 can include a base 128 coupled to an upper assembly 130 via an extendable support pole 126 (e.g., a center pole). The extendable support pole 126 can be moved between an extended position and a compressed position, such as via a hydraulic actuator, a pneumatic actuator, a crank, or an electrical linear actuator, although other mechanisms can be used. In some cases, the extendable support pole 126 can be a hydraulic actuator or can include a hydraulic actuator. In some cases, a lever for opening the hydraulic actuator to permit compression of the hydraulic actuator can be positioned at or adjacent a hand bar 158.

The platform 104 can include hooks 132 on the upper assembly 130 to support one or more IV bags 106, which can be coupled to a patient 102 via IV tubing 108. In some cases, the IV tubing 108 can pass through an IV pump 134, which can be coupled to the upper assembly 130. The upper assembly 130 can include an adjustable bar 146 that can be vertically adjusted to support the IV pump 134 at a desired position.

In some cases, the platform 104 can include a tray assembly 120 including a deployable tray portion 154 and a fixed tray portion 152. The deployable tray portion 120 can be foldable about a hinge (e.g., a piano hinge or other such hinge) to move between a stored position and a deployed position. In the deployed position, the deployable tray portion 120 can support items, such as a meal 118. In some cases, one or more latches (e.g., side latches) can be used to secure the deployable tray portion 120 in a deployed position. In some cases, the deployable tray portion 120 can partially or fully fit within the fixed tray portion 152 and be extended from the fixed tray portion 152 during deployment, optionally without folding.

The platform 104 can include a hand bar 158 located at or near the tray assembly 120. For example, the hand bar 158 can be located in a plane parallel a top surface of the tray assembly 120, such as a plane coplanar with the top surface of the tray assembly 120, a plane that intersects the tray assembly 120, a plane above the tray assembly 120, or a plane below the tray assembly 120. The hand bar 158 can be positioned at a height suitable for grasping by the patient 102 during ambulation with the platform 104, such as depicted in FIG. 1. The hand bar 158 can be coupled to the support pole 126 or the tray assembly 120. The distance between the hand bar 158 and the base 128 can be adjusted via adjustment of the support pole 126 between an extended position and a compressed position.

In some cases, the platform 104 can include one or more accessory hooks to support a chest tube collection device 110 (e.g., a Pleur-evac® system) at a desired height. The chest tube collection device 110 can be coupled to the patient 102 via a chest tube 112. In some cases, the tray system can include one or more hooks to support the chest tube collection device 110. Since the tray system is height-adjustable, supporting the chest tube collection device 110 by the tray system can facilitate adjustment of the chest tube collection device 110 to a desired vertical height for each individual patient. In some cases, the hook supporting the chest tube collection device 110 can have a width greater than 2 cm, 3 cm, 4 cm, 5 cm, 6 cm, 7 cm, 8 cm, 9 cm, or 10 cm. Such a large width can facilitate securing the chest tube collection device 110 by a handle of the chest tube collection device 110 and in a generally level alignment. In some cases, the hook can be vertically adjustable with respect to the tray assembly 120. In some cases, the hook can be coupled to the tray assembly 120 at the fixed tray portion 152.

In some cases, the base of the platform 104 can include a surface and/or a gas canister retention strap 124 to secure a gas canister 114 to the platform 104. The gas canister retention strap 124 can be coupled to the support pole 126 such that the gas canister 114 can rest on the base 128 (e.g., on a leg of base 128) or on a footrest that is at least partially supported by base 128. In some cases, a clamp or other securement feature can be used instead of a gas canister retention strap 124. The gas canister 114 can be coupled to a patient 102 via tubing 116.

In some cases, a catheter collection bag hook 115 can be installed on the platform 104, such as on the support pole 126, at a location between the base 128 and the tray assembly 120. The position of the catheter collection bag hook 115 can facilitate proper drainage of a catheter collection bag, such as a urine collection bag of a Foley catheter.

The platform 104 can include a friction reducing element to facilitate translating the base 128 along a floor. In some cases, such as depicted in FIG. 1, the friction reducing element takes the form of casters coupled to legs of base 128. Other arrangements and mechanisms can be used, such as wheels, low-friction materials, bearings, and the like. The platform 104 can be used by a patient 102 as an ambulation assistant, to help the patient 102 walk in direction 122. Certain aspects and features of the disclosed platform 104 permit a patient 102 using the platform 104 to have a clear line of sight in direction 122 when ambulating in direction 122. Additionally, certain aspects and features of the disclosed platform 104 permit various equipment (e.g., IV bags 106, IV pumps 134, chest tube collection devices 110, catheter collection bags, gas canisters 114, and the like) to be supported by the platform 104 in positions that leave the patient 102 with a clear line of sight in direction 122 when ambulating in direction 122 (e.g., not blocking the patient's view during ambulation).

Figure 2:
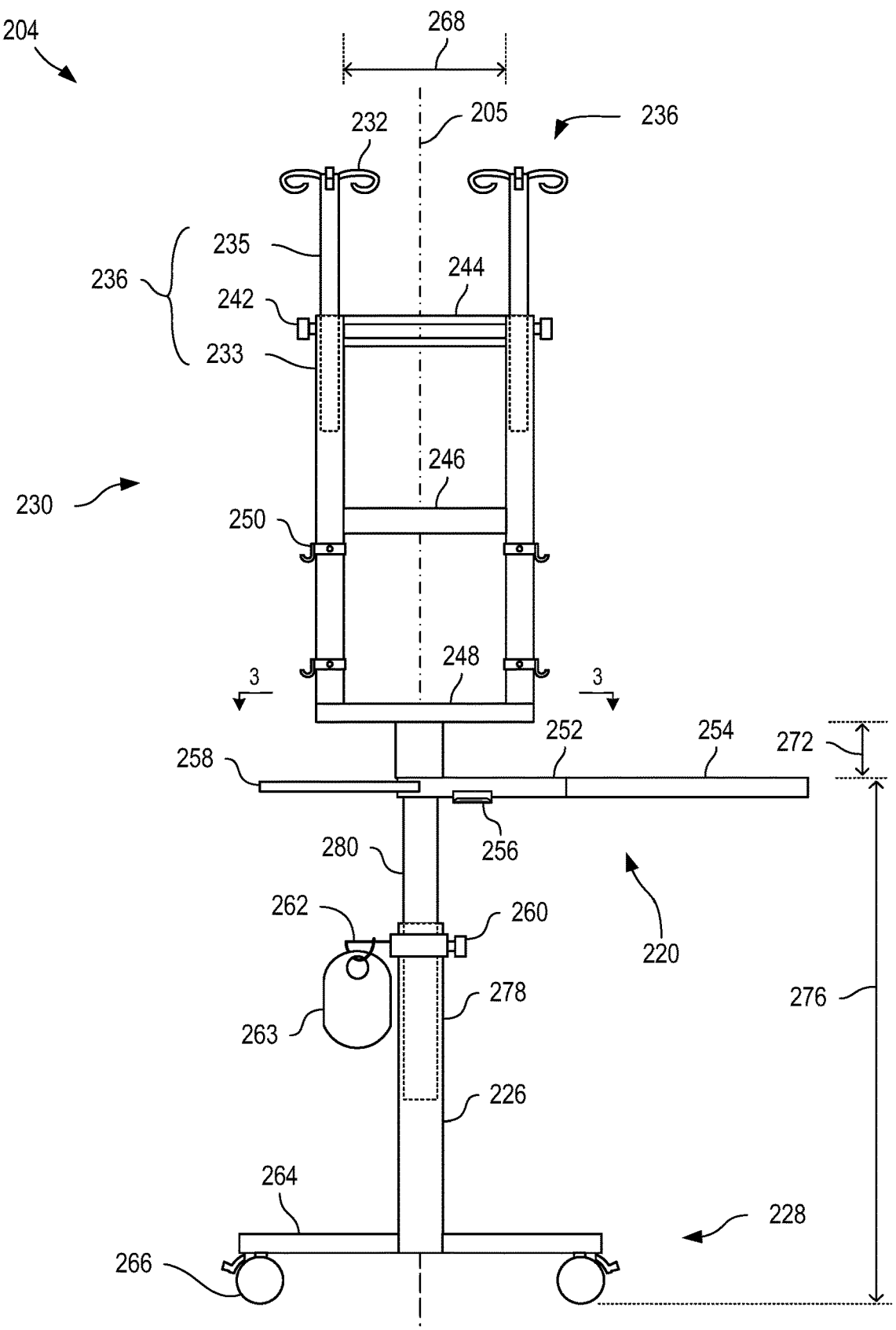
FIG. 2 is a side view of a multifunctional medical platform according to certain aspects of the present disclosure.

FIG. 2 is a side view of a multifunctional medical platform 204 according to certain aspects of the present disclosure. Platform 204 can be or can be similar to platform 104 of FIG. 1. The platform 204 can include an upper assembly 230 coupled to a base 228 via an extendable support pole 226. The extendable support pole 226 can extend by movement of an inner pole 280 within an outer pole 278. For example, the lower portion of extendable support pole 226 can be an outer pole 278 having an opening at a top end, within which the inner pole 280 can fit. Translation of the inner pole 280 longitudinally within the outer pole 278 can result in extension or compression of the support pole 226. In some cases, support pole 226 can be or can include a hydraulic actuator (e.g., hydraulic cylinder). Such a hydraulic actuator can be pressurized to support the weight of the inner pole 280 and any permanent fixtures attached to the inner pole 280 (e.g., upper assembly 230, hand bar 258, and tray assembly 220). Thus, extension and compression of the support pole 226 when the platform 204 is unloaded can require minimal force, permitting extension and compression of the support pole 226 when loaded (e.g., with an IV bag and IV pump) to be performed with relatively small force (e.g., as compared to extending and compressing the support pole 226 if no hydraulic actuator were used). Generally, the longitudinal center of support pole 226 is collinear with the longitudinal centerline 205 (e.g., vertical centerline as depicted in FIG. 2) of the platform 204, although that need not always be the case.

The base can include multiple legs 264 extending distally out from the longitudinal centerline 205 of the platform 204, with casters 266 coupled at the distal ends of the legs 264. The casters 266 can facilitate translation of the platform 204 along a surface, such as a floor. Any suitable caster 266 can be used. For example, any combination of swivel casters, straight casters, locking casters, non-locking casters, and the like can be used to support base 228. Generally, support pole 226 is positioned in line with a geometric center and/or center of gravity of base 228, although that need not always be the case. In some cases, the distance between the longitudinal centerline 205 of the platform 204 and the distal ends of legs 264 is at or approximately 12 inches (30.48 cm).

In some cases, a catheter collection hook 262 can be coupled to the support pole 226, such as to an outer pole 278 of the support pole 226. The catheter collection hook 262 can be coupled to the support pole 226 via an adjustment collar. Adjustment collar 260 can use a knob to tighten or loosen the adjustment collar 260 on the support pole 226. Thus, by loosening the adjustment collar 260, the catheter collection hook 262 can be raised or lowered along the support pole 226 until a desired position is reached, at which time the adjustment collar 260 can be tightened to secure the catheter collection hook 262 in place. In some cases, the catheter collection hook 262 can be adjustable to move up and down a length of the support pole 226 between the base 228 and the tray assembly 220, such as a length that extends between the base 228 and the top of outer pole 278. This adjustment can facilitate proper placement of a catheter collection bag 263 for proper drainage, especially for patients of different heights or a patient in a seated position (e.g., in a chair or wheelchair).

A tray assembly 220 can be coupled to the support pole 226, such as coupled to inner pole 280. The tray assembly 220 can include a fixed tray portion 252 and a deployable tray portion 254. The deployable tray portion 254 can be movable between a deployed position (as shown) and a stowed position. In some cases, the deployable tray portion 254 can be folded, rotated, retracted, or otherwise manipulated to move from the deployed position to the stowed position. A hook 256 for a chest tube collection device such as that in FIG. 1 is attached to the tray portion 254. The tray assembly 220 can be coupled to the support pole 226 such that the tray height 276 (e.g., the distance between the floor or the bottom of casters 266 and the top surface of the fixed tray portion 252 or deployable tray portion 254) increases and decreases with extension and compression of the support pole 226, respectively. In some cases, the amount of extension of the support pole 226 is such that the tray height 276 is adjustable between at or approximately 28 inches (71.12 cm) and at or approximately 40 inches (101.6 cm). As used herein for tray height 276, as well as other suitable distances, the term "approximately" is inclusive of values within 1%, 2%, 3%, 4%, 5%, 6%, 7%, 8%, 9%, 10%, 11%, 12%, 13%, 14%, and/or 15% of the given value.

A hand bar 258 can be coupled to the support pole 226, such as coupled directly to the support pole 226 at the inner pole 280 or coupled to the support pole 226 via the tray assembly 220. The hand bar 258 can extend out from the longitudinal centerline 205 of the platform for any suitable distance. In some cases, the hand bar 258 extends for a distance greater than that of the upper assembly 230. In some cases, the hand bar 258 extends for a distance greater than that of the base 228. However, as depicted in FIG. 2, the hand bar 258 is shown as extending for a distance slightly less than that of the base 228. The hand bar 258 can be coupled such that extension and compression of the support pole 226 results in increasing and decreasing the distance between the hand bar 258 and the floor, respectively. Thus, the hand bar 258 can be naturally positioned at a level that can be easily grasped to provide support and that facilitates controlling movement of the platform 204. If needed, the support pole 226 can be raised or lowered as needed to place the hand bar 258 at a desired height for a particular user.

Upper assembly 230 can be coupled to the support pole 226, such as via a spacer. In some cases, the spacer can be coupled directly to the support pole 226 or can be coupled to the tray assembly 220. The spacer can help establish a gap 272 between a bottom of the upper assembly 230 and a top surface of the tray assembly 220. Generally, the spacer can establish a gap 272 that is at or approximately 8 inches (20.32 cm), although other distances can be used.

Upper assembly 230 can include one or more vertical poles 236, such as a pair of vertical poles 236 as depicted in FIG. 2. Each vertical pole 236 can include a lower pole 233 and an upper pole 235. The upper pole 235 can fit within the lower pole 233 and be locked in place by knob 242. Thus, the total length of the vertical pole 236 can be adjusted by retracting the upper pole 236 into the lower pole 233 or extending the upper pole 236 out of lower pole 233, then locking the upper pole 236 in place with the knob 242. One or more intravenous hooks 232 can be located at an upper end of the vertical pole 236 (e.g., at an upper end of upper pole 236). The intravenous hooks 232 can receive an IV bag. Adjustment of the total length of the vertical pole 236 can permit the IV bag to be moved to a desired position for purposes of providing desired infiltration of IV fluids, to a desired position for purposes of maintaining a clear line of sight while ambulating with the platform 204, or to a desired position for purposes of changing or otherwise handling the IV bag. In some cases, the vertical pole 236 can further include one or more supplemental hooks 250, which can each be vertically adjustable via an adjustable collar. Such supplemental hooks 250 can be positioned on the lower pole 233 and can be used to retain additional medical equipment, such as collection or supply bags, tubes, medical devices, as well as non-medical equipment (e.g., bags or personal possession of the patient).

Each vertical pole 236 can extend upwards from a lower support 248. The lower support 248 can take the form of a bar, plate, circular disk, or other shape. To provide additional support, a support bar 244 can be coupled between the vertical poles 236, such as at upper ends of the lower poles 233. The support bar 244 can be a flat bar designed to provide additional stiffening support to the vertical poles 233, as well as to provide a location for mounting medical equipment, such as IV pumps. In some cases, an adjustable bar 246 is provided between the vertical poles 236 at a level between the support bar 244 and the lower support 248. The adjustable bar 246 can be vertically adjustable, such as to increase or decrease a distance between the lower support 248 and adjustable bar 246. In some cases, adjustable bar 246 can be especially suitable as a mounting site for certain equipment, such as IV pumps. In some cases, the spaces or voids between the vertical poles 236 and between the lower support 248 and adjustable bar 246 and between the adjustable bar 246 and support bar 244 can be especially useful for mounting medical equipment. The adjustability of the adjustable bar 246 can provide flexibility to mount desired medical equipment in a safe and convenient manner.

In some cases, the lower pole 233 can have a length that is at or approximately 30 inches (76.2 cm). In some cases, the upper pole 235 can extend from the lower pole 233 by a distance that is at or approximately 14 inches (35.56 cm). The clearance distance 268 between the vertical poles 236 can be at or approximately 12 inches (30.48 cm). The distance between the top of the lower support 248 and top of the support bar 244 can be at or approximately 30 inches (76.2 cm). In some cases, the lower pole 233 can have a diameter of at or approximately 1 inch (2.54 cm) and the upper pole 235 can have a diameter of at or approximately 0.75 inches (1.905 cm). In some cases, the support pole 226 can have an outer pole 278 that has a diameter of at or approximately 3 inches (7.62 cm) and an inner pole 280 that has a diameter of at or approximately 2.5 inches (6.35 cm). In some cases, the casters 266 are approximately 2.5 inch (6.35 cm) full swivel casters.

Figure 3:
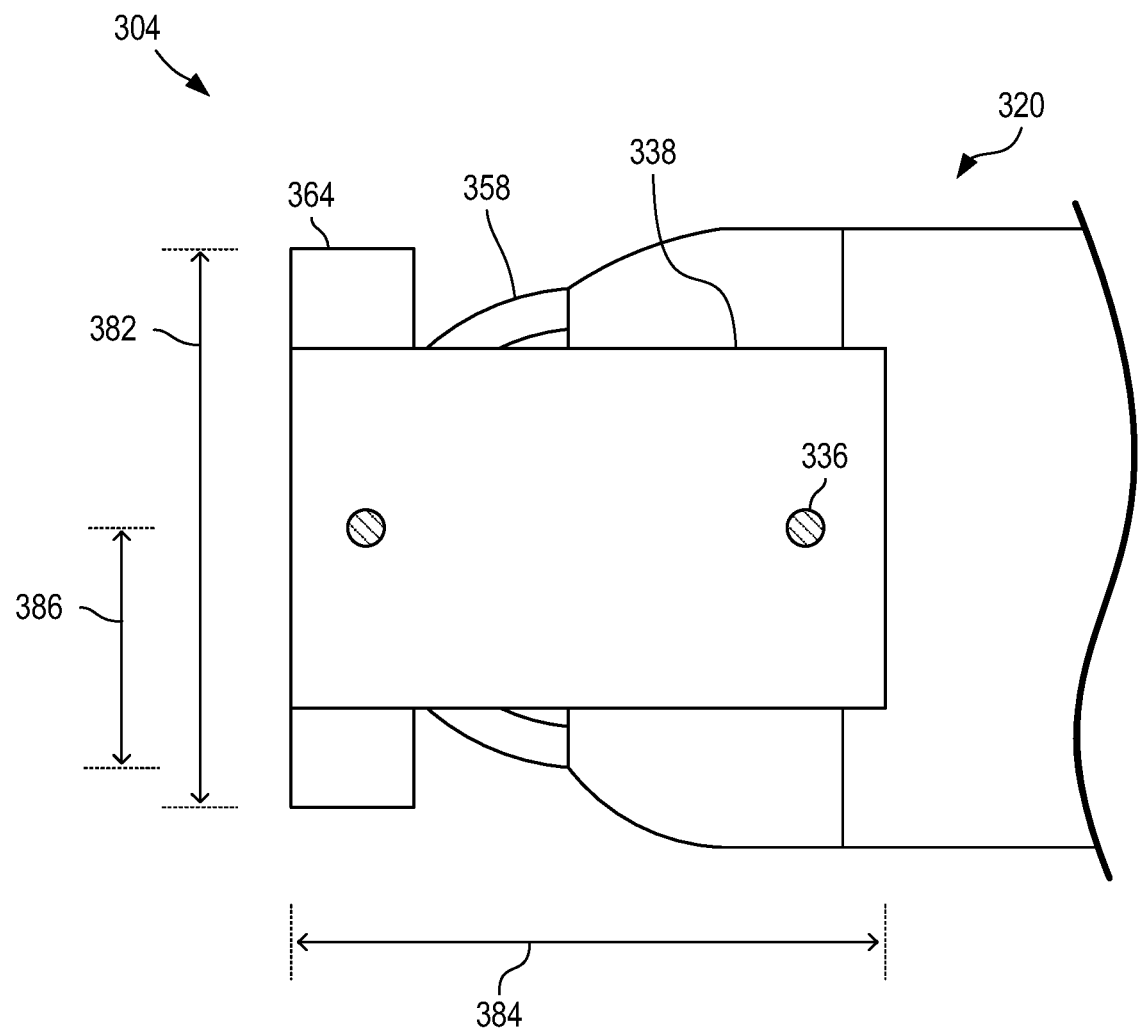
FIG. 3 is a cutaway top view of a multifunctional medical platform taken along line 3:3 of FIG. 2 according to certain aspects of the present disclosure.

FIG. 3 is a cutaway top view of a multifunctional medical platform 304 taken along line 3:3 of FIG. 2 according to certain aspects of the present disclosure. Platform 304 can be similar to platform 204 of FIG. 2. From the top view, some of the legs 364 of the base are seen below a lower support 338 of the upper assembly. Vertical poles 336 are seen extending upwards (e.g., out of the page as depicted in FIG. 3) from the lower support 338. Below lower support 338, a hand bar 358 is supported on one side of the support pole and the tray assembly 320 is supported on an opposite side of the support pole. In some cases, however, the hand bar 358 and tray assembly 320 are not positioned opposite the support pole from one another.

The hand bar 358 can take the form of a semi-circular shape (e.g., a round tube curved in a circular shape, such as a torus) and can extend from the longitudinal centerline of the platform 304 by distance 386. When a taking the form of a semi-circular shape, distance 386 can be a radius. In some cases, such as if the hand bar 358 is positioned vertically above or below the tray assembly 320, the hand bar 358 can take the form of a fully circular shape.

In some cases, the width 382 and/or length 384 of the base can be at or approximately 24 inches (60.96 cm). In some cases, the casters can be coupled to the leg 364 by housings, such as housings having lengths and widths that are at or approximately 4 inches (10.16 cm). In some cases, the hand bar 358 can be a tube having a diameter of at or approximately 0.75 inches (1.905 cm). In some cases, the width 382 of the tray assembly 320 (e.g., taken in an up-down direction as depicted in FIG. 3) can be at or approximately 16 inches (40.64 cm) or greater. In some cases, the length of the tray assembly 320 (e.g., taken in a left-right direction as depicted in FIG. 3) can be at or approximately 25 inches (63.5 cm) or greater when the deployable tray portion is in the deployed position.

As depicted in FIG. 3, the base includes legs 364 that are coupled by together by a crossbar to form an H shape (e.g., with the legs 364 forming the arms of the H and the crossbar forming the center line of the H). As such, the legs 364 and crossbar define two U shaped voids, one on either side of the crossbar (e.g., a U shaped void pointing toward the top of the page and a U shaped void pointing towards the bottom of the page, as viewed in FIG. 3). As depicted in FIG. 3, the hand bar 358 extends from the support pole such that a lateral centerline of the hand bar 358 (e.g., a line extending through the center of the hand bar 358 in a direction towards the left side of the page as viewed in FIG. 3) is perpendicular a plane passing through the lateral centerline of the U shaped voids (e.g., a plane extending in and out of the page and up and down the page, passing through the center of the U shaped voids). Likewise, the tray assembly 320 is depicted as extending from the support pole such that a lateral centerline of the tray assembly 320 (e.g., a line extending through the center of the tray assembly 320 in a direction towards the right side of the page as viewed in FIG. 3) is perpendicular the plane passing through the lateral centerline of the U shaped voids. However, in some cases, the hand bar 358 and/or tray assembly 320 can be oriented such that one or both extend from the support pole such that their respective lateral centerline is parallel the lateral centerline of the U shaped voids (e.g., in such cases, the hand bar 358 and/or tray assembly 320 would be rotated 90° or 270° around the longitudinal axis of the support pole from the position depicted in FIG. 3).

Figure 4:
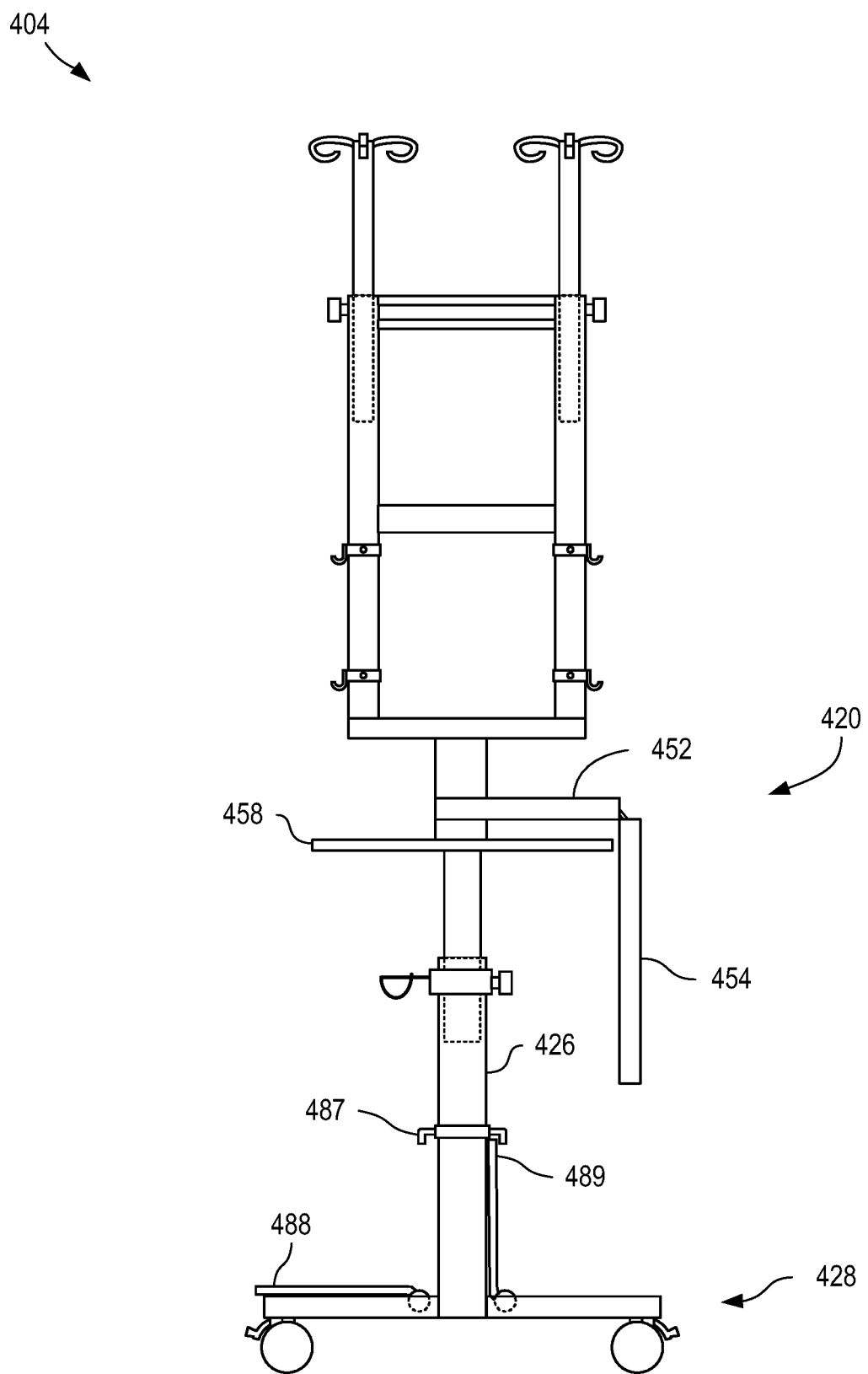
FIG. 4 is a side view of a multifunctional medical platform with a deployable tray portion in a stowed position according to certain aspects of the present disclosure.

FIG. 4 is a side view of a multifunctional medical platform 404 with a deployable tray portion 454 in a stowed position, according to certain aspects of the present disclosure. Platform 404 can be similar to platform 104 of FIG. 1.

Platform 404 includes a hand bar 458 that is circular in shape and extends through a full 360° sweep around the support pole 426. Because the hand bar 458 extends through a full 360° sweep around the support pole 426, it is positioned below the tray assembly 420 (e.g., below the fixed tray portion 452). In some cases, however, the hand bar 458 can be positioned above the tray assembly 420 (e.g., above the fixed tray portion 452).

The tray assembly 420 of the platform 404 is shown in a stowed state. The fixed tray portion 452 remains coupled to the support pole 426, however the deployable tray portion 454 is shown in the stowed position. Since the deployable tray portion 454 depicted in FIG. 4 is a foldable deployable tray portion, in the stowed position, the deployable tray portion 454 has folded, rotating about an axis of rotation, such that the upper surface of the deployable tray portion 454 is now in a plane perpendicular or approximately perpendicular with the floor. The deployable tray portion 454 can remain in the stowed position through the use of gravity or can be secured in place through the use of a clip, magnet, strap, hook and loop fastener, or other securement feature. The deployable tray portion 454 can be coupled to the fixed tray portion 452 via a hinge, such as a piano hinge. When the deployable tray portion 454 is moved to the deployed position, it can be locked in place through the use of any suitable locking mechanism, such as one or more latches located on a side of the tray assembly 420.

Platform 404 is depicted as having a pair of deployable footrests, 488, 489. The first deployable footrest 488 is depicted in a deployed position. In the deployed position, the deployable footrest 488 is at least partially supported by the base 428 (e.g., a leg of the base 428) such that force applied to a top surface (e.g., a footrest surface) of the deployable footrest 488 will be conducted through the base 428. Deployable footrest 489 is depicted in a stowed position, having been rotated up, about an axis of rotation. In the stowed position, the deployable footrest 489 can be at or approximately vertical, such as having its footrest surface being at or approximately in a plane perpendicular to the floor. In some cases, the deployable footrest 489 can be secured in place through the use of a footrest hook 487, however any securement feature can be used, such as a latch, magnet, hook and loop fastener, strap, or the like. Thus, deployable footrests 488, 489 can be deployed or stowed as needed. In some cases, deployable footrest 488 can be used as a support surface for supporting at least a portion of the weight of a gas canister.

Figure 5:
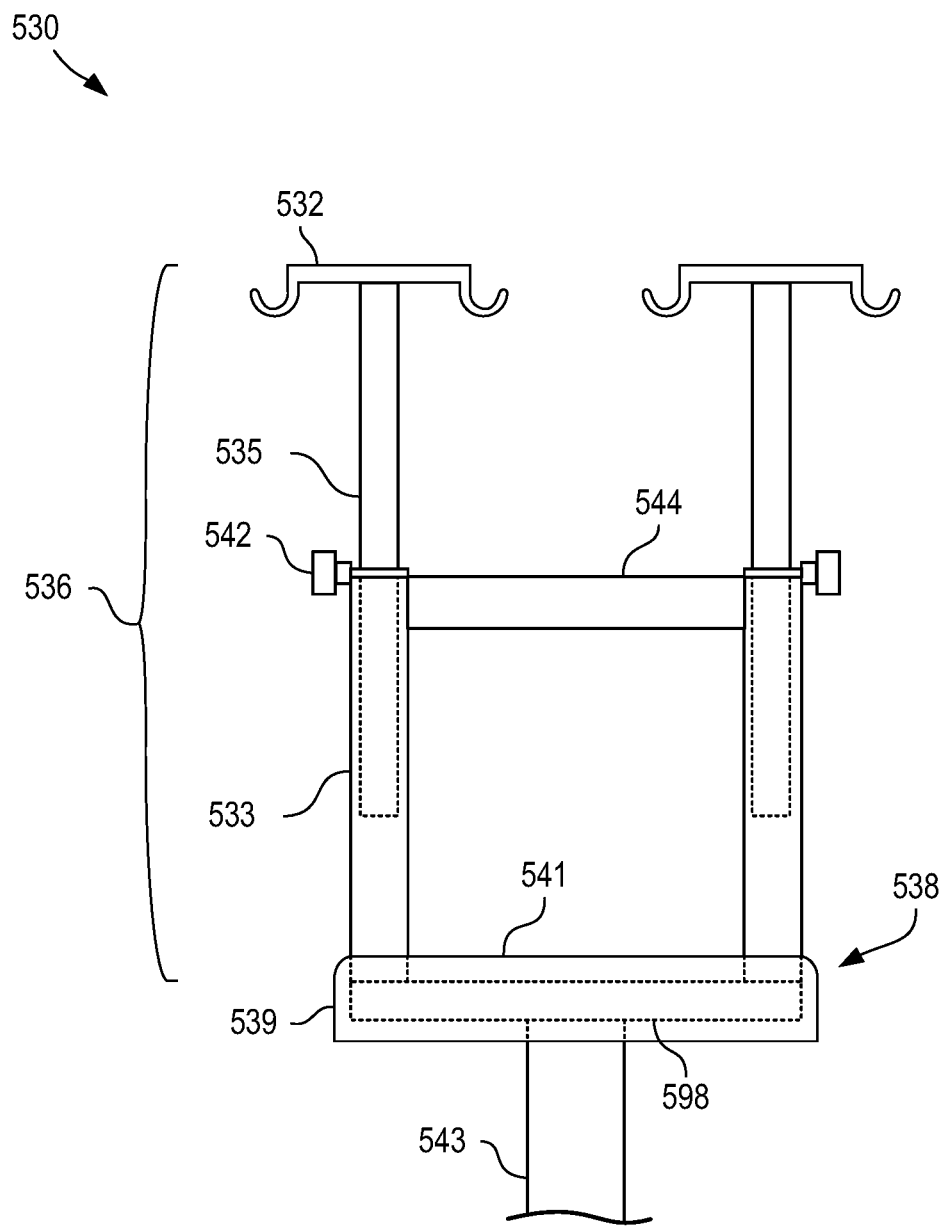
FIG. 5 is a close-up side view of an upper assembly of a multifunctional medical platform according to certain aspects of the present disclosure.

FIG. 5 is a close-up side view of an upper assembly 530 of a multifunctional medical platform according to certain aspects of the present disclosure. Upper assembly 530 can be similar to upper assembly 130 of FIG. 1.

Upper assembly 530 can include a pair of vertical poles 536 extending upwards (e.g., towards the top of the page in FIG. 5) from a support surface 538. The support surface 538 can include a crossbar 598 over which a support surface cap 541 is placed. The support surface cap 541 can provide a flat and/or larger surface for supporting equipment and other items thereon. The support surface cap 541 can further include a lip 539 extending down and around the crossbar 598. The lip 539 can extend below the crossbar, such that a bottom surface of the support surface cap 541 is positioned between the base and a bottom surface of the crossbar 598. The crossbar 598 can be coupled to the support pole, such as via a spacer 543. Spacer 543 can provide a gap between the bottom of the upper assembly 530 (e.g., the bottom of the support surface 538) and the top of the tray assembly. In some cases, the crossbar 598 can be directly coupled to the support pole. In some cases, the support surface cap 541 can be coupled to the crossbar 598, although in some cases the support surface cap 541 merely rests upon the crossbar 598. In some cases, the crossbar 598 can have a square or rectangular cross section, although that need not always be the case.

Each of the pair of vertical poles 536 can be coupled to the support surface 538, such as at opposite ends of the crossbar 598, although that need not always be the case. In such cases, however, the support surface cap 541 can include apertures or voids through which each of the pair of vertical poles 536 can pass through.

The upper assembly 530 is depicted as including a single support bar 544 positioned at a top end of the bottom pole 533 of the vertical pole 536. The top pole 535 is extendable out of the bottom pole 533, and securable in place with collar 542. In some cases, however, other securement mechanisms can be used in place of collar 542, such as a pin or electronic actuator.

The vertical pole 536 is depicted with a IV hook 532 of a different style than IV hook 132 of FIG. 1. Each of the vertical poles 536 can be individually adjustable to move their respective IV hooks 532 to different vertical heights.

Figure 6:
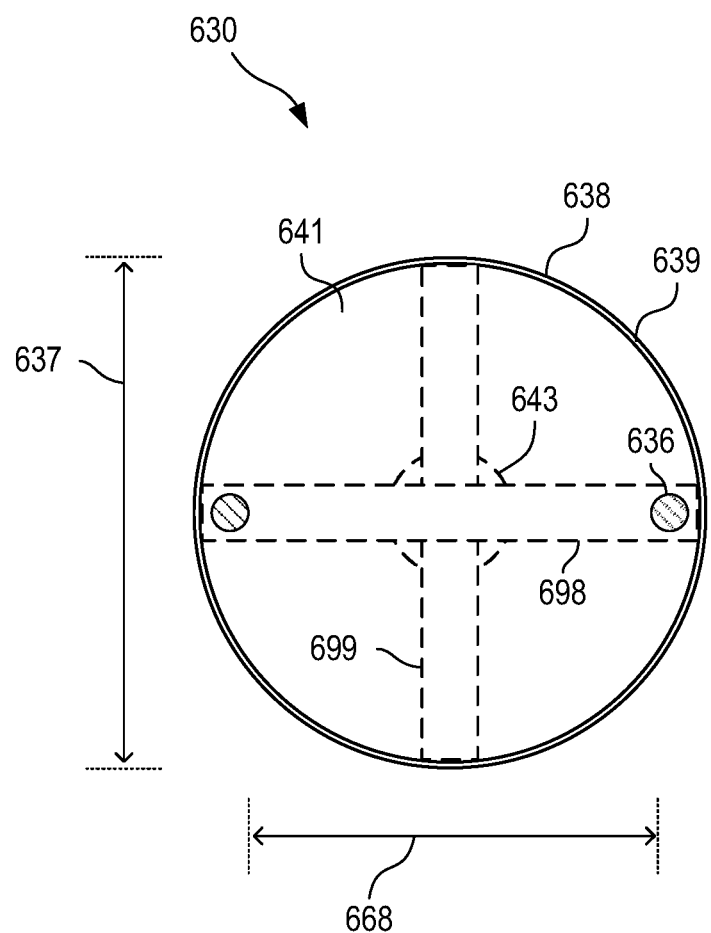
FIG. 6 is a top cross-sectional view of an upper assembly of a multifunctional medical platform according to certain aspects of the present disclosure.

FIG. 6 is a top cross-sectional view of an upper assembly 630 of a multifunctional medical platform according to certain aspects of the present disclosure. Upper assembly 630 can be or be similar to upper assembly 530 of FIG. 5. The cross-sectional view of FIG. 5 can be taken along a plane parallel the floor and just above the support surface 638.

Vertical poles 636 are depicted as extending up from the support surface 638, from crossbar 698. One or more supplemental support bars 699 can be coupled to crossbar 698 to provide additional support for the support surface cap 641. The support surface cap 641 is shown as having a generally circular shape, with a lip 639 at the circumference. In some cases, support surface cap 641 can additionally have an upward facing (e.g., out of the page as depicted in FIG. 6) lip to stop objects placed on the support surface cap 641 from rolling over the edge of the support surface cap 641. Crossbar 698 can be coupled to spacer 643, or directly to a support pole.

The support surface 638 can have a diameter 637 that is greater than a clearance distance 668 between the vertical poles 636 plus the diameters of the vertical poles 636, although that need not always be the case. In some cases, the clearance distance 668 can be at or approximately 12.5 inches (31.75 cm). In some cases, the vertical poles 636 can have a diameter of at or approximately 1.25 inches (3.175 cm).

In some cases, the support surface cap 641 can be an especially useful location to support a chest tube collection device, an IV pump, and/or a pump for a chest tube collection device.

Figure 7:
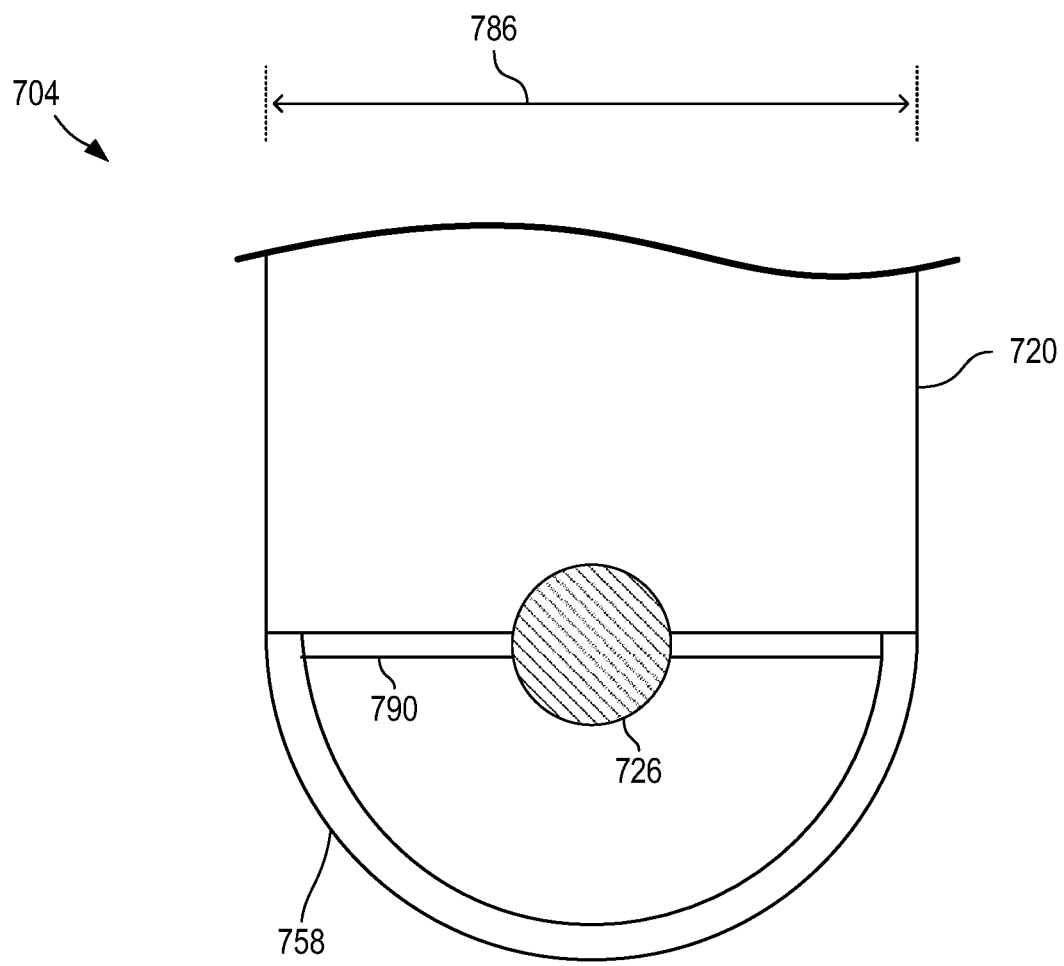
FIG. 7 is a cutaway top view of a multifunctional medical platform depicting a hand bar and tray assembly according to certain aspects of the present disclosure.

FIG. 7 is a cutaway top view of a portion of a multifunctional medical platform 704 depicting a hand bar 758 and tray assembly 720 according to certain aspects of the present disclosure. The platform 704 can be or be similar to platform 104 of FIG. 1.

The hand bar 758 can be coupled to the support pole 726 via one or more radial bars 790. In some cases, the hand bar 758 can be coupled to the support pole 726 via the tray assembly 720 additionally or instead of via one or more radial bars 790. In some cases, the hand bar 758 can have a width 786 (e.g., a diameter) that is at or approximately 18 inches (45.72 cm). In some cases, the tray assembly 720 can have a width that is at or approximately the same width 786 of the hand bar 758. The hand bar 758 can be in the form of a curved tube having a circular or generally circular cross section. The hand bar 758 can be especially useful for easy grasping when ambulating with the platform 704, as well as serving as a convenient attachment point to hang objects (e.g., additional equipment or personal effects) or attach lines (e.g., IV tubes, drainage tubes, catheter tubes, oxygen tubes, and the like.

Figure 8:
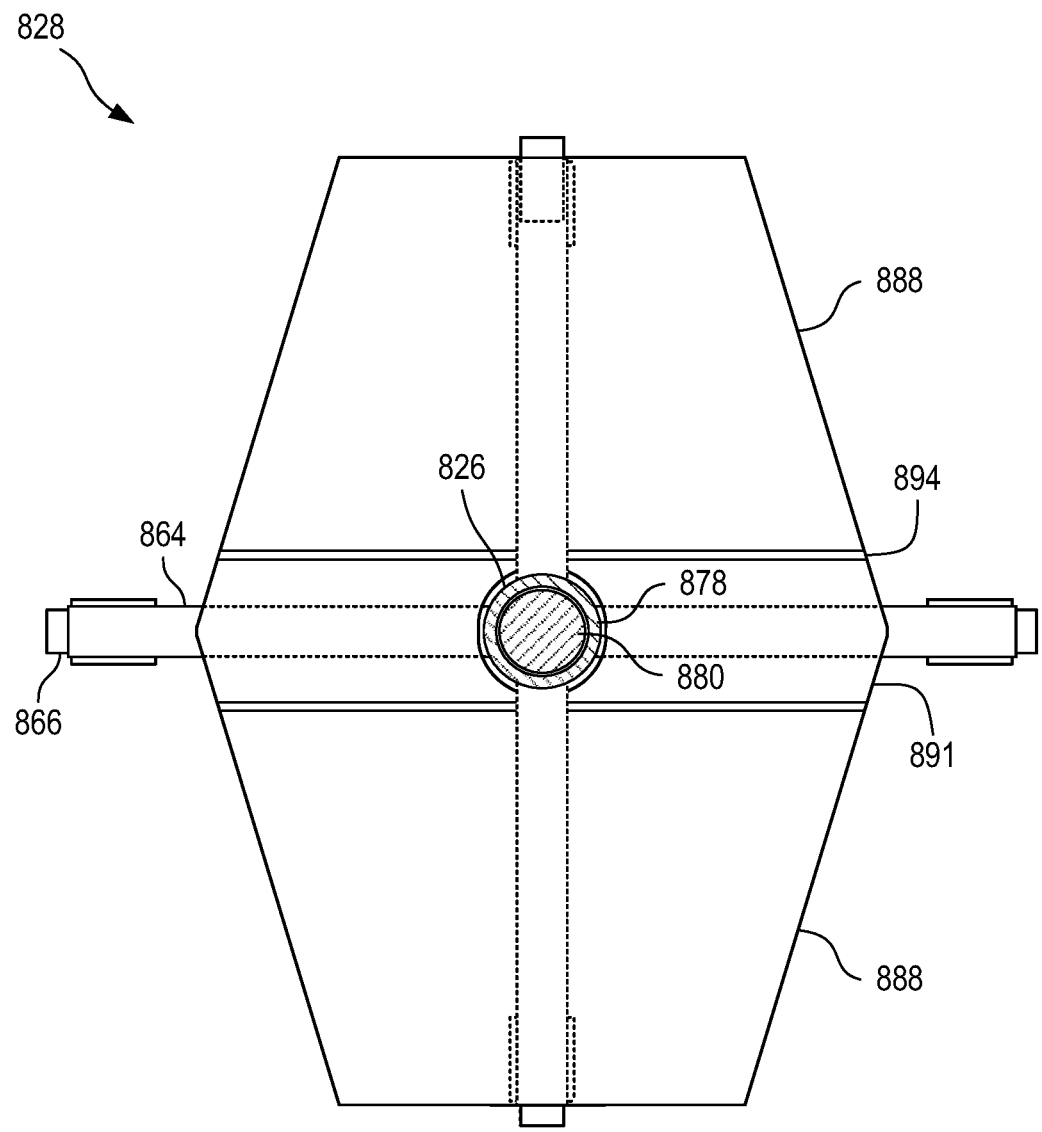
FIG. 8 is a cutaway top view of a base of a multifunctional medical platform with a deployed footrest according to certain aspects of the present disclosure.

FIG. 8 is a cutaway top view of a base 828 of a multifunctional medical platform with deployed footrests 888 according to certain aspects of the present disclosure. Base 828 can be similar to base 128 of FIG. 1. The cutaway top view is taken along a plane parallel the floor and just below the top of the outer pole 878 of the support pole 826. The inner pole 880 is seen in an opening or recess of outer pole 878.

The base 828 of FIG. 8 is depicted as having a cross-shaped leg pattern, with each leg 864 extending from a center of the base 828. Each leg 864 can extend from the center of the base 828 in a direction such that the angular distance between each leg 864 is the same (e.g., at 90° angles when four legs 864 are used, but at 72° angles when five legs are used). Casters 866 are seen under the legs 864 at distal ends of the legs 864.

The deployable footrests 888 are seen in a deployed position. In the deployed position, the deployable footrests 888 rest upon the legs 864, permitting force applied to the top of the deployable footrests 888 to be carried through to the legs 864 of base 828. The deployable footrests 888 of FIG. 8 are depicted as hinging around hinges 894. Thus, to move the deployable footrests 888 to a stowed position, the deployable footrests 888 are rotated around hinges 894. The hinges 894 coupled the deployable footrests 888 to a center plate 891, which is coupled to legs 864 and/or support pole 826.

In some cases, however, the deployable footrests 888 can be coupled to the support pole 826 and/or legs 864 in other fashions, and can be moved between deployed and stowed positions in other fashions. In some cases, the footrest can be a non-deployable footrest, or a fixed footrest, always positioned in an equivalent of the deployed position (e.g., a plate similar in shape to deployable footrests 888 of FIG. 8, but without any hinges 864).

Figure 9:
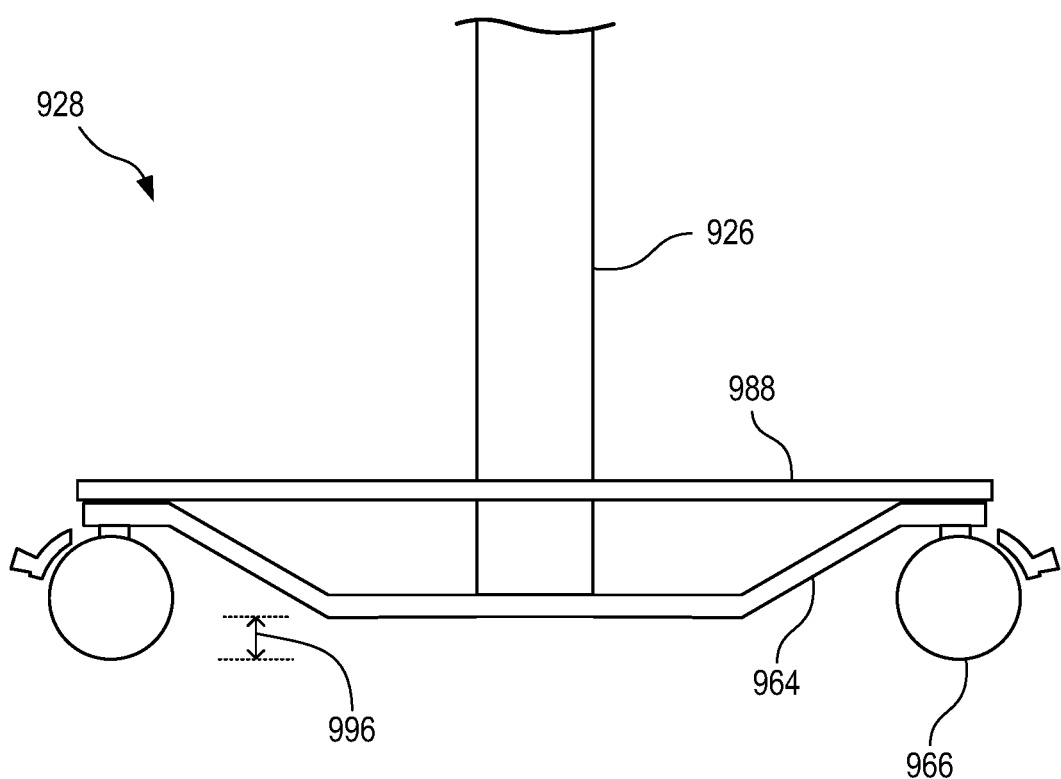
FIG. 9 is a side view of a base of a multifunctional medical platform according to certain aspects of the present disclosure.

FIG. 9 is a side view of a base 928 of a multifunctional medical platform according to certain aspects of the present disclosure. Base 928 can be or be similar to base 828 of FIG. 8. A footrest 988 is depicted, being supported by legs 964 of base 928.

Base 928 is seen having vertically angled, or recessed, legs 964, which vary in height above the floor from the center of the base 928 to the outside edges of base 928. Legs 964 support casters 966 at their distal ends, at which point the leg is in a plane parallel to the floor. However, moving proximally (e.g., towards the center of the base 928 or a centerline of the base 928), the leg 964 angles towards the floor (e.g., at or approximately at a 60° slope), before returning to a plane parallel to the floor. This style of base 928 can permit sufficiently large casters to be used, while keeping the bottom of the base 928 at a low height 996 above the floor. Support pole 926 is depicted coupled to legs 964 where the legs 964 are at their lowest position. In some cases, the height 996 of the legs 964 at their lowest positions can be at or approximately 1.5 inches (3.81 cm) above the floor. Thus, casters 966 having diameters greater than height 996 can be used.

The benefit of such a base 928 include moving the center of gravity of the platform close to the floor, as well as creating a recess in the base 928 suitable for other uses, such as to hold weight (e.g., to further lower the center of gravity of the platform and otherwise stabilize the platform) or other equipment.

As used herein, the terms "tube" and "bar" are inclusive of any cross-sectional shape suitable for the given purpose, such as square, rectangular, circular, oval-shaped, elongated circle, ovoid, contoured, or the like.

The foregoing description of the embodiments, including illustrated embodiments, has been presented only for the purpose of illustration and description and is not intended to be exhaustive or limiting to the precise forms disclosed. Numerous modifications, adaptations, and uses thereof will be apparent to those skilled in the art. Specifically, a multifunctional medical platform as disclosed herein can include any combination of elements and features as described above with reference to FIGS. 1-9. For example, one embodiment of a multifunctional medical platform might include a chest tube collection hook and a catheter collection bag hook, whereas a different embodiment of a multifunctional medical platform might include a chest tube collection hook and an adjustable bar for supporting an IV pump. Any suitable combinations can be used.

As used below, any reference to a series of examples is to be understood as a reference to each of those examples disjunctively (e.g., "Examples 1-4" is to be understood as "Examples 1, 2, 3, or 4").

Example 1 is a medical platform, comprising: a base having a plurality of legs; a set of casters, each caster of the set of casters being coupled at a distal region of a respective leg of the plurality of legs of the base; a support pole extending vertically from the base, the support pole movable between a compressed position and an extended position; an upper assembly coupled to the support pole, the upper assembly having a plurality of vertical poles extending away from the base and a plurality of hooks coupled to top ends of the plurality of vertical poles; and a tray assembly coupled to the support pole between the base and the upper assembly, the tray assembly having a stationary tray portion and a deployable tray portion, the deployable tray portion movable between a stowed position and a deployed position; a catheter collection bag hook coupled to one of the support pole and the tray assembly at or below the stationary tray portion, wherein the catheter collection bag hook is positioned to maintain a catheter collection bag at or below a waist level of a patient during ambulation; and a hand bar coupled to one of the support pole and the tray assembly.

Example 2 is the medical platform of example(s) 1, wherein the base further includes a central bar having a first end and a second end, wherein the support pole extends from the central bar, wherein the plurality of legs includes a first pair of legs and a second pair of legs, wherein the first pair of legs extends distally and collinearly from the first end of the central bar, and wherein the second pair of legs extends distally and collinearly from the second end of the central bar.

Example 3 is the medical platform of example(s) 1 or 2, further comprising: a deployable footrest movable between a deployed position and a stowed position; and a footrest securement feature coupled to the support pole, wherein the footrest securement feature is usable to secure the footrest in the stowed position.

Example 4 is the medical platform of example(s) 3, wherein the deployable footrest includes a footrest surface for supporting a foot of a patient when the footrest is in the deployed position, wherein the deployable footrest is movable such that the footrest surface is in a substantially vertical position when the deployable footrest is in the stowed position; and wherein the deployable footrest, when in the deployed position, contacts at least one of the plurality of legs to pass force applied to the footrest surface to the at least one of the plurality of legs.

Example 5 is the medical platform of example(s) 1-4, wherein the tray assembly is coupled to the support pole such that movement of the support pole from the compressed position to the extended position increases the distance from the base to the tray assembly.

Example 6 is the medical platform of example(s) 1-5, wherein a distance between an outer edge of the hand bar and support pole is greater than a distance between the support pole and the distal end of each of the plurality of legs.

Example 7 is the medical platform of example(s) 1-6, wherein the support pole comprises: an inner pole positioned within an outer pole; and a hydraulic actuator usable to extend and retract the inner pole out from and into the outer pole to move the support pole between the compressed position and the extended position.

Example 8 is the medical platform of example(s) 1-7, wherein the hand bar forms a semi-circular shape opposite the support pole from the tray assembly.

Example 9 is the medical platform of example(s) 1-8, further comprising a chest tube collection device hook coupled to the stationary tray portion of the tray assembly, wherein the chest tube collection device hook is shaped to receive a handle of a chest tube collection device.

Example 10 is the medical platform of example(s) 1-9, wherein the catheter collection bag hook is coupled to the support pole using an adjustable collar, wherein the adjustable collar permits the catheter collection bag hook to be raised or lowered along a length of the support pole between the base and the tray assembly.

Example 11 is the medical platform of example(s) 1-10, further comprising a gas canister retention strap positioned on the support pole between the base and the tray assembly for securing a gas canister to the support pole.

Example 12 is the medical platform of example(s) 1-11, wherein each vertical pole of the plurality of vertical poles of the upper assembly includes an upper pole positioned within an opening of a lower pole, the lower pole positioned between the upper pole and the base, wherein the upper pole is movable within the opening to adjust a length of the vertical pole, and wherein at least one of the plurality of hooks is coupled to a top end of the upper pole.

Example 13 is the medical platform of example(s) 1-12, wherein the upper assembly includes: a crossbar coupled to the support pole, wherein at least one of the plurality of vertical poles is coupled to the crossbar; and a circular support surface positioned on the crossbar, the circular support surface having a diameter greater than a length of the crossbar, wherein the circular support surface includes a lip that extends towards the base such that a bottom surface of the lip is vertically positioned between a bottom surface of the crossbar and the base.

Example 14 is a medical platform system, comprising: a base having a friction reducing element to facilitate translating the base along a floor; an extendable support pole coupled to the base; a hand bar coupled to the support pole to facilitate translating the base along the floor; a deployable tray assembly coupled to the support pole such that extension of the extendable support pole increases a distance between the deployable tray assembly and the base; and an upper assembly coupled to the support pole, the upper assembly including at least one vertical pole, the at least one vertical pole having a hook positioned at an upper end of the vertical pole for receiving an intravenous bag.

Example 15 is the medical platform system of example(s) 14, wherein a distance between the upper assembly and the deployable tray assembly remains constant during extension of the extendable support pole.

Example 16 is the medical platform system of example(s) 14 or 15, wherein the at least one vertical pole is extendable such that a distance between the hook and the deployable tray assembly is adjustable separately from a distance between the deployable tray assembly and the base.

Example 17 is the medical platform system of example(s) 14-16, wherein the base includes: a central bar having a first end and a second end, wherein the support pole is perpendicularly coupled to the central bar; and a set of legs extending perpendicular to the central bar at opposite ends of the central bar, wherein the set of legs and the central bar form a pair of opposing U shape voids, wherein a first void of the pair of opposing U shape voids is positioned opposite the central bar from a second void of the pair of opposing U shape voids; wherein the friction reducing element includes a set of casters, wherein each caster of the set of casters is positioned at a distal end of a respective leg of the set of legs.

Example 18 is the medical platform system of example(s) 17, wherein the hand bar forms a semi-circular shape that extends over the first void of the pair of opposing U shape voids, wherein a center axis of the semi-circular shape is laterally centered above a center axis of the first void of the pair of opposing U shape voids; and wherein a center axis of the tray assembly is laterally centered above a center axis of the second void of the pair of opposing U shape voids.

Example 19 is the medical platform system of example(s) 14-17, wherein the at least one vertical pole comprises a pair of vertical poles, and wherein the tray assembly extends from the support pole in a direction parallel a line between the pair of vertical poles.

Example 20 is the medical platform system of example(s) 14-19, further comprising a deployable footrest movable between a deployed position and a stowed position, wherein the deployable footrest includes a footrest surface for supporting a foot of a patient when the footrest is in the deployed position, wherein the deployable footrest is movable such that the footrest surface is in a substantially vertical position when the deployable footrest is in the stowed position; wherein the deployable footrest is securable in the stowed position by a footrest securement feature coupled to the support pole; and wherein the deployable footrest, when in the deployed position, contacts the base to pass force applied to the footrest surface to the base.

What is claimed is:

1. A medical platform, comprising:
   a base having a plurality of legs;
   a set of casters, each caster of the set of casters being coupled at a distal region of a respective leg of the plurality of legs of the base;
   a support pole extending vertically from the base, the support pole movable between a compressed position and an extended position;
   an upper assembly coupled to the support pole, the upper assembly having a plurality of vertical poles extending away from the base and a plurality of hooks coupled to top ends of the plurality of vertical poles; and
   a tray assembly coupled to the support pole between the base and the upper assembly, the tray assembly having a stationary tray portion and a deployable tray portion, the deployable tray portion movable between a stowed position and a deployed position;
   a catheter collection bag hook coupled to one of the support pole and the tray assembly at or below the stationary tray portion, wherein the catheter collection bag hook is positioned to maintain a catheter collection bag at or below a waist level of a patient during ambulation;
   a hand bar coupled to one of the support pole and the tray assembly;
   a deployable footrest movable between a deployed position and a stowed position; and
   a footrest securement feature coupled to the support pole, wherein the footrest securement feature is usable to secure the footrest in the stowed position.

2. The medical platform of claim 1, wherein the deployable footrest includes a footrest surface for supporting a foot of a patient when the footrest is in the deployed position, wherein the deployable footrest is movable such that the footrest surface is in a substantially vertical position when the deployable footrest is in the stowed position; and wherein the deployable footrest, when in the deployed position, contacts at least one of the plurality of legs to pass force applied to the footrest surface to the at least one of the plurality of legs.

3. The medical platform of claim 1, wherein the tray assembly is coupled to the support pole such that movement of the support pole from the compressed position to the extended position increases the distance from the base to the tray assembly.

4. The medical platform of claim 1, wherein a distance between an outer edge of the hand bar and support pole is greater than a distance between the support pole and a distal end of each of the plurality of legs.

5. The medical platform of claim 1, wherein the support pole comprises:
   an inner pole positioned within an outer pole; and
   a hydraulic actuator usable to extend and retract the inner pole out from and into the outer pole to move the support pole between the compressed position and the extended position.

6. The medical platform of claim 1, wherein the hand bar forms a semi-circular shape opposite the support pole from the tray assembly.

7. The medical platform of claim 1, further comprising a chest tube collection device hook coupled to the stationary tray portion of the tray assembly, wherein the chest tube collection device hook is shaped to receive a handle of a chest tube collection device.

8. The medical platform of claim 1, wherein the catheter collection bag hook is coupled to the support pole using an adjustable collar, wherein the adjustable collar permits the catheter collection bag hook to be raised or lowered along a length of the support pole between the base and the tray assembly.

9. The medical platform of claim 1, further comprising a gas canister retention strap positioned on the support pole between the base and the tray assembly for securing a gas canister to the support pole.

10. The medical platform of claim 1, wherein each vertical pole of the plurality of vertical poles of the upper assembly includes an upper pole positioned within an opening of a lower pole, the lower pole positioned between the upper pole and the base, wherein the upper pole is movable within the opening to adjust a length of the vertical pole, and wherein at least one of the plurality of hooks is coupled to a top end of the upper pole.

11. The medical platform of claim 1, wherein the upper assembly includes:
   a crossbar coupled to the support pole, wherein at least one of the plurality of vertical poles is coupled to the crossbar; and
   a circular support surface positioned on the crossbar, the circular support surface having a diameter greater than a length of the crossbar, wherein the circular support surface includes a lip that extends towards the base such that a bottom surface of the lip is vertically positioned between a bottom surface of the crossbar and the base.

12. A medical platform system, comprising:
a base having a friction reducing element to facilitate translating the base along a floor;
an extendable support pole coupled to the base;
a hand bar coupled to the support pole to facilitate translating the base along the floor;
a deployable tray assembly coupled to the support pole such that extension of the extendable support pole increases a distance between the deployable tray assembly and the base;
an upper assembly coupled to the support pole, the upper assembly including at least one vertical pole, the at least one vertical pole having a hook positioned at an upper end of the vertical pole for receiving an intravenous bag; and
a deployable footrest movable between a deployed position and a stowed position, wherein the deployable footrest includes a footrest surface for supporting a foot of a patient when the footrest is in the deployed position, wherein the deployable footrest is movable such that the footrest surface is in a substantially vertical position when the deployable footrest is in the stowed position; wherein the deployable footrest is securable in the stowed position by a footrest securement feature coupled to the support pole; and wherein the deployable footrest, when in the deployed position, contacts the base to pass force applied to the footrest surface to the base.

13. The medical platform system of claim 12, wherein a distance between the upper assembly and the deployable tray assembly remains constant during extension of the extendable support pole.

14. The medical platform system of claim 12, wherein the at least one vertical pole is extendable such that a distance between the hook and the deployable tray assembly is adjustable separately from a distance between the deployable tray assembly and the base.

15. The medical platform system of claim 12, wherein the base includes:
a central bar having a first end and a second end, wherein the support pole is perpendicularly coupled to the central bar; and
a set of legs extending perpendicular to the central bar at opposite ends of the central bar, wherein the set of legs and the central bar form a pair of opposing U shape voids, wherein a first void of the pair of opposing U shape voids is positioned opposite the central bar from a second void of the pair of opposing U shape voids;
wherein the friction reducing element includes a set of casters, wherein each caster of the set of casters is positioned at a distal end of a respective leg of the set of legs.

16. The medical platform system of claim 15, wherein the hand bar forms a semi-circular shape that extends over the first void of the pair of opposing U shape voids, wherein a center axis of the semi-circular shape is laterally centered above a center axis of the first void of the pair of opposing U shape voids; and wherein a center axis of the tray assembly is laterally centered above a center axis of the second void of the pair of opposing U shape voids.

17. The medical platform system of claim 12, wherein the at least one vertical pole comprises a pair of vertical poles, and wherein the tray assembly extends from the support pole in a direction parallel a line between the pair of vertical poles.

18. A medical platform, comprising:
a base having a plurality of legs;
a set of casters, each caster of the set of casters being coupled at a distal region of a respective leg of the plurality of legs of the base;
a support pole extending vertically from the base, the support pole movable between a compressed position and an extended position;
an upper assembly coupled to the support pole, the upper assembly having a plurality of vertical poles extending away from the base and a plurality of hooks coupled to top ends of the plurality of vertical poles; a crossbar coupled to the support pole, wherein at least one of the plurality of vertical poles is coupled to the crossbar; and a circular support surface positioned on the crossbar, the circular support surface having a diameter greater than a length of the crossbar, wherein the circular support surface includes a lip that extends towards the base such that a bottom surface of the lip is vertically positioned between a bottom surface of the crossbar and the base;
a tray assembly coupled to the support pole between the base and the upper assembly, the tray assembly having a stationary tray portion and a deployable tray portion, the deployable tray portion movable between a stowed position and a deployed position;
a catheter collection bag hook coupled to one of the support pole and the tray assembly at or below the stationary tray portion, wherein the catheter collection bag hook is positioned to maintain a catheter collection bag at or below a waist level of a patient during ambulation; and
a hand bar coupled to one of the support pole and the tray assembly.

* * * * *